US006458546B1

(12) United States Patent
Baker

(10) Patent No.: US 6,458,546 B1
(45) Date of Patent: Oct. 1, 2002

(54) METHODS AND REAGENTS FOR PRESERVATION OF DNA IN BODILY FLUIDS

(75) Inventor: Tony Baker, Sonora, CA (US)

(73) Assignee: Sierra Diagnostics, Inc., Palo Alto, CA (US)

(*) Notice: Subject to any disclaimer, the term of this patent is extended or adjusted under 35 U.S.C. 154(b) by 0 days.

(21) Appl. No.: 09/882,871

(22) Filed: Jun. 15, 2001

Related U.S. Application Data

(63) Continuation of application No. 09/805,785, filed on Mar. 13, 2001, which is a continuation of application No. 09/185,402, filed on Nov. 3, 1998, now abandoned, which is a continuation-in-part of application No. 08/988,029, filed on Dec. 10, 1997, now abandoned.

(51) Int. Cl.[7] .......................... C12Q 1/68; A61K 35/14; A61K 35/22; C07H 21/04
(52) U.S. Cl. ..................... 435/6; 424/529; 424/545; 536/23.1
(58) Field of Search ............... 435/6; 424/529, 424/545; 536/23.1, 127

(56) References Cited

U.S. PATENT DOCUMENTS 4,915,941 A * 4/1990 Vigouroux et al. ........ 424/85.5

FOREIGN PATENT DOCUMENTS

WO   WO 93/03167   * 8/1992
WO   WO 95/35390   * 6/1995

OTHER PUBLICATIONS

Y-K Hong et al., Journal of Applied Phycology, "DNA extraction conditions from Porphyra perforata using LiCl," 1995, 7:pp.101–107.*
H Ahern, website:www.the-scientist.library.upenn.edu, "Biochemical, Reagent Kits Offer Scientists Good Return on Investment," Jul. 1995, pp. 1–5.*

* cited by examiner

Primary Examiner—W. Gary Jones
Assistant Examiner—Jehanne Souaya
(74) Attorney, Agent, or Firm—Nicholas P. Triano, III; Mintz, Levin, Cohn, Ferris, Glovsky and Popeo, P.C.

(57) ABSTRACT

A method and system are provided for preserving nucleic acids in a bodily fluid, such as urine, blood, blood serum, and amniotic fluid. The preservative includes an amount of a divalent metal chelator selected from ethylenediaminetetraacetic acid (EDTA), [ethylenebis(oxyethylenenitrilo)] tetraacetic acid (EGTA) and 1,2-bis(2-aminophenoxy) ethane-N,N,N', N'-tetraacetic acid (BAPTA), or salts thereof in the range of from about 0.001M to 0.1M; and an amount of at least one chelator enhancing component selected from lithium chloride, guanidine, sodium salicylate, sodium perchlorate, and sodium thiocyanate in the range of from about 0.1M to 2M.

22 Claims, 14 Drawing Sheets

METHODS AND REAGENTS FOR PRESERVATION OF DNA IN BODILY FLUIDS

RELATED APPLICATIONS

This application is a continuation of application Ser. No. 09/805,785 filed on Mar. 13, 2001, which in turn is a continuation of application Ser. No. 09/185,402 filed on Nov. 3, 1998, now abandoned, which is a continuation-in-part application Ser. No. 08/988,029 filed on Dec. 10, 1997 now abandoned. The contents of all of the aforementioned application(s) are hereby incorporated by reference.

BACKGROUND OF THE INVENTION

The present disclosure relates generally to the field of DNA analysis. More particularly, the present disclosure relates to methods, preservative reagents and systems for preserving DNA in bodily fluids for subsequent testing and analysis.

Modern testing and treatment procedures have successfully reduced the prevalence and severity of many infectious diseases. For example, sexually-transmitted disease (STD) clinics regularly screen and treat patients for such diseases as gonorrhea and Syphilis. It is now well-known to identify infectious agents such as gonococci by analyzing a DNA sample. A genetic transformation test (GTT), such as Gonostat® (Sierra Diagnostics, Inc., Sonora, Calif.), can be used to detect gonococcal DNA in specimens taken from the urethra of men, and the cervix and anus of women, according to Jaffe H W, Kraus S J, Edwards T A, Zubrzycki L. *Diagnosis of gonorrhea using a genetic transformation test on mailed clinical specimens*, J Inf Dis 1982; 146:275–279. A similar finding was also published in Whittington W L, Miller M, Lewis J, Parker J, Biddle J, Kraus S. *Evaluation of the genetic transformation test,*. Abstr Ann Meeting Am Soc Microbiol 1983; p. 315.

The GTT is a test for biologically active or native DNA. For example, the Gonostat(3) GTT can be used to detect DNA such as gonococcal DNA in urine specimens. The Gonostat® assay uses a test strain, *N. Gonorrhoeae*, ATCC 31953. This test strain is a mutant that is unable to grow into visible colonies on chocolate agar at 37° C. in 5% $CO_2$. Gonococcal DNA extracted from clinical material can restore colony growth ability to this test strain. The Gonostat® assay is discussed in Zubrzycki L, Weinberger S S, *Laboratory diagnosis of gonorrhea by a simple transformation test with a temperature-sensitive mutant of Neisseria gonorrhoeae*. Sex Transm Dis 1980; 7:183–187.

It is not always possible to immediately test a patient for the presence of such an infectious agent. For example, clinical laboratories are not readily found in many rural or underdeveloped areas. In such circumstances, it is necessary to transport patient test specimens to a laboratory for analysis. It is therefore desirable to preserve such specimens for subsequent analysis with a GTT or other testing procedure.

Urine specimens are frequently practical and convenient for use in diagnoses of an infection, such as gonorrhea A urine specimen can be collected by a patient, therefore avoiding the invasion of privacy and discomfort accompanying collection of other specimens, such as blood specimens, urethral cultures, or cervical cultures. Collection of a urine specimen by the patient also reduces the work load of the staff in the clinic or office.

DNA culture results of urine from males are quite sensitive when the urine is cultured within two hours of collection. Such results can approach 92% to 94%, or even 100%, as described in Schachter J. *Urine as a specimen for diagnosis of sexually transmitted diseases*. Am J Med 1983; 75:93–97. However, the culture results of urine from females are not very reliable, even when cultured within two hours. According to Schachter, only 47% to 73% of female urine cultures are positive relative to the culture results of cervical and anal specimens. Furthermore, it is known that culture results from any anatomic site are not 100% sensitive. (See, for example, Johnson D W, Holmes K K, Kvale P A, Halverson C W, Hirsch W P. *An evaluation of gonorrhea casefinding in the chronically infected male*. Am J Epidemiol 1969; 90:438–448; Schmale J D, Martin J E, Domescik G. *Observations on the culture diagnosis of gonorrhea in women*. JAMA 1969; 210:213–314; Caldwell J G, Price E V, Pazin G J, Cornelius E C. *Sensitivity and reproducibility of Thayer-Martin culture medium in diagnosing gonorrhea in women*. Am J Gynecol 1971; 109:463–468; Kieth L, Moss W, Berger G S. *Gonorrhea detection in a family planning clinic: A cost-benefit analysis of 2,000 triplicate cultures*. Am J Obstet Gynecol 1975; 121:399–403; Luciano A A, Grubin L. *Gonorrhea screening*. JAMA 1980; 243:680–681; Goh B T, Varia K B, Ayliffe P F, Lim F K. *Diagnosis of gonorrhea by gram-stained smears and cultures in men and women: Role of the urethral smear*. Sex Trans Dis 1985; 12:135–139.

Currently, urine specimens must be tested quickly for the presence of naked gonococcal DNA. Naked DNA is intact double stranded DNA which is released from viable gonococci. Such naked DNA can be found in the urine of an infected patient. However, enzymes in urine rapidly destroy any DNA present in the specimen. The DNA is either denatured, broken into single strands or totally destroyed by the enzymatic activity. This destruction of the DNA can effectively inactivate the naked gonococcal DNA for purposes of testing.

In a test such as the GTT, inactivation beyond the limits of detection is determined by the inherent genetic needs for select gene sequences of the Gonostat mutant strain used in the Gonostat test. For example, the Gonostat transformation assay is a very sensitive measurement tool for nucleic acid protection. In the GTT, the Gonostat organism must have approximately 1 picogram of native DNA to transform. This amount is equal to the presence of approximately 30 gonorrhea bacteria in an inoculum. The average clinical infection has $10^3$–$10^5$ such organisms.

The destruction of DNA by enzyme activity in a urine specimen increases with time. For example, naked gonococcal DNA in a urine specimen that is stored in excess of two hours is inactivated beyond the limits of detection of the GTT. As a result, the testing of urine specimens for DNA is very time-sensitive. For example, DNA-based tests such as the polymerase chain reaction (PCR), the ligase chain technology ($LC_x$) test of Abbott Laboratories, Abbott Park, Ill., and the GTT all must be performed on a urine specimen within approximately two hours. FIG. 1 is a graph of DNA concentration in unpreserved urine according to the prior art, demonstrating DNA destruction over time. The gonococcal DNA concentrations of ten different types of urine specimens were tested using a GTT at hourly intervals, commencing one hour from time of inoculation. Approximately 200 transformants were counted at the one hour measurement. However, for all specimens, the number of transformants declined by more than 100% within one hour of this initial measurement. The number of transformants approached zero within the two hours of the initial measurement, FIG. 2 is a graph of eight day serial data on unpreserved urine according to the prior art, further illustrating DNA destruction in unpreserved samples. Approximately seven transformants were counted at the one day measurement. However, by the second day, testing indicated that the biologically active DNA in the unpreserved urine had been totally destroyed by enzyme activity.

Tests such as the GTT can also be used to detect DNA in such bodily fluids and excretions as blood, blood serum, amniotic fluid, spinal fluid, conjunctival fluid, salivary fluid, vaginal fluid, stool, seminal fluid, and sweat. FIG. 3 is a graph of DNA concentration in unpreserved serum according to the prior art, demonstrating DNA destruction over time. The gonococcal DNA concentrations of normal and abnormal serum of both male and female were tested at hourly intervals, commencing from the time of inoculation. Approximately 100 transformants were counted at the one hour measurement. However, for all specimens, the number of transformants declined by more than 100% within three hours of this initial measurement. The number of transformants approached zero within the eight hours of the initial measurement.

Another test that can be used to identify DNA in a bodily fluid specimen is the PCR test. PCR testing uses discrete nucleic acid sequences and therefore can be effective even in the absence of intact DNA. FIG. 4 is a graph of PCR detection of MOMP Chlamydia in unpreserved urine according to the prior art, demonstrating DNA destruction over time. In PCR testing of an unpreserved urine specimen, four PCR absorbances were observed one hour after the addition of the MOMP Chlamydia. However, the number of PCR absorbances declined 100%, to two, when tested at two hours, and to zero by the third hour. This testing indicates that, even though PCR testing doesn't require intact DNA, the enzymatic activity of urine rapidly destroys even discrete nucleic acid sequences 45 within approximately three hours.

Unfortunately, practical and effective techniques for preserving DNA in certain bodily fluids have not been readily available. For example, one method used to deactivate urine enzymes is heating. In an experiment, urine was heated for five minutes in a boiling water bath (100° C.) and then cooled. Naked DNA and DNA released from gonococcal cells that were subsequently added to this urine were not deactivated. This suggests that the deoxyribonuclease component in urine is a protein(s).

However, heating can denature DNA that is already present in the urine specimen, including gonococcal DNA, as well as the DNA of *Haemophilus influenzoe* and *Bacillus subtilis*. Thus, heating is not an appropriate method for preserving a patient urine specimen to test for the presence of such DNA.

In other known DNA assay systems, it is known to add detergents or other chemicals to assist in the detection of DNA. For example, in the DNA assay system described in Virtanen M, Syvanen A C, Oram J, Sodurlund H, Ranki M. *Cytomegalovirus in urine: Detection of viral DNA by sandwich hybridization*. J Clin Microbiol. 1984; 20:1083–1088, sarkosyl was used to detect cytomegalovirus (CMV) in urine by hybridization. In Boom R, Sol C J A, Salimans M M M, Jansen C L, Wertheim-van Dillen P M E, van der Noordaa J. *Rapid and simple method for purification of nucleic acids*. J Clin Microbiol 1990; 28:495–503, guanidinium chloride in urine was used to purify nucleic acids as assayed by gel electrophoresis. Although the reason for their use in these studies was not stated, the chemicals inactivated the deoxyribonuclease activity in urine that would have interfered with those assay systems.

It would therefore be advantageous to provide a method and system for preserving DNA in a bodily fluid such as urine, blood, blood serum, amniotic fluid, spinal fluid, conjunctival fluid, salivary fluid, vaginal fluid, stool, seminal fluid, and sweat, such that the efficacy of the DNA assays, e.g., the PCR, $LC_x$, and the GTT is optimized.

SUMMARY OF THE INVENTION

The present disclosure relates to methods, systems and reagents for preserving nucleic acids, e.g., DNA and RNA, in bodily fluids. In one advantageous embodiment, the invention is directed to the preservation of nucleic acids in urine. In another advantageous embodiment, the invention enables the molecular assay of nucleic acids in other bodily fluids and excretions, such as blood, blood serum, amniotic fluid, spinal fluid, conjunctival fluid, salivary fluid, vaginal fluid, stool, seminal fluid, and sweat to be carried out with greater sensitivity, as the methods and preservatives of the invention have been found to surprisingly increase the signal obtained with such nucleic acid testing methods as polymerase chain reaction (PCR), $LC_x$, and genetic transformation testing (GTT). An unexpected advantage of the invention is that hybridization in such nucleic acid testing methods is improved compared to when such nucleic acid testing methods are carried out without employing the present invention.

In an embodiment, the invention relates to methods of preserving a nucleic acid in a fluid such as a bodily fluid, including providing a nucleic acid preservative solution comprising an amount of a divalent metal chelator selected from ethylenediaminetetraacetic acid (EDTA), [ethylenebis(oxyethylenenitrilo)]tetraacetic acid (EGTA) and 1,2-bis(2-aminophenoxy)ethane-N,N,N',N'-tetraacetic acid (BAPTA), or salts thereof; and an amount of at least one chelator enhancing component selected from lithium chloride, guanidine, sodium salicylate, sodium perchlorate, and sodium thiocyanate; and adding the nucleic acid preservative to the fluid, e.g., a bodily fluid. The amount of the divalent metal chelator is generally in the range of from about 0.001M to 0.1M, and the amount of the chelator enhancing component is generally in the range of from about 0.1M to 2M. The amount of chelator enhancing component is more desirably at least 1M in the preservative solution, and the divalent metal chelator is desirably present in an amount of at least about 0.01M.

In another embodiment, the invention relates to nucleic acid preservative solutions comprising an amount of a divalent metal chelator selected from EDTA, EGTA and BAPTA, and salts thereof, and an amount of at least one chelator enhancing component selected from lithium chloride, guanidine, sodium salicylate, sodium perchlorate, and sodium thiocyanate. The amount of the divalent metal chelator is generally in the range of from about 0.001M to 0.1M, and the amount of the chelator enhancing component is generally in the range of from about 0.1M to 2M. The amount of chelator enhancing component is more desirably at least 1M in the preservative solution, and the divalent metal chelator is desirably present in an amount of at least about 0.01M.

The methods and preservatives of the invention may further include an amount of at least one enzyme inactivating component such as manganese chloride, sarkosyl, or sodium dodecyl sulfate, generally in the range of about 0–5% molar concentration.

In yet another aspect the invention relates to a method of improving the signal response of a molecular assay of a test sample, including providing a nucleic acid preservative solution comprising an amount of a divalent metal chelator selected from EDTA, EGTA and BAPTA, and salts thereof; and an amount of at least one chelator enhancing component selected from lithium chloride, guanidine, sodium salicylate, sodium perchlorate, and sodium thiocyanate; adding the nucleic acid preservative to a test sample to provide a preserved test sample; extracting molecular analytes of interest, e.g., DNA, from the preserved test sample, and conducting a molecular assay on the extracted molecular analytes of interest. The amount of the, divalent metal chelator is generally in the range of from about 0.001M to 0.1M, and the amount of the chelator enhancing component is generally in the range of from about 0.1M to 2M. The chelator enhancing component is more advantageously one or more of sodium perchlorate, sodium thiocyanate, guanidine, and lithium chloride. The amount of chelator enhancing component is more desirably at least 1M in the preservative solution, and the divalent metal chelator is desirably present in an amount of at least about 0.01M. Signal response is believed to be enhanced in part due to enhanced hybridization as a result of the use of the reagents of the present invention.

Use of the methods and preservatives disclosed herein eliminate enzymatic destruction of the nucleic acid of interest in the bodily fluid. The preservative can optionally be provided in solid or gaseous forms. While the methods and preservatives of the invention are useful in preserving all types of nucleic acids, e.g., RNA and DNA, including human DNA, and bacterial, fungal, and viral DNA, the invention is especially advantageous for use in preserving prokaryotic DNA, e.g., gonococcal DNA, DNA of *Haemophilus influenzoe* and *Bacillus subtilis*. Nucleic acids in a bodily fluid are preserved for testing for a significantly longer period of time than that permitted by the prior art. While the maximum time between collecting, mailing, and testing patient specimens is expected to be approximately six days, the invention is effective beyond that period of time.

A further aspect of the invention relates to methods of improving hybridization of nucleic acids, including contacting a test nucleic acid with a nucleic acid preservative solution comprising an amount of a divalent metal chelator selected from ethylenediaminetetraacetic acid (EDTA), ethylenebis(oxyethylenenitrilo)]tetraacetic acid (EGTA) and 1,2-bis(2-aminophenoxy)ethane-N,N,N',N'-tetraacetic acid (BAPTA), or salts thereof in the range of from about 0.001M to 0.1M; and an amount of at least one chelator enhancing component selected from lithium chloride, guanidine, sodium salicylate, sodium perchlorate, and sodium thiocyanate in the range of from about 0.1M to 2M, such that a test solution is formed; and contacting the test solution with a target nucleic acid under conditions favorable for hybridization, such that hybridization occurs.

DETAILED DESCRIPTION OF THE INVENTION

Figure 1:
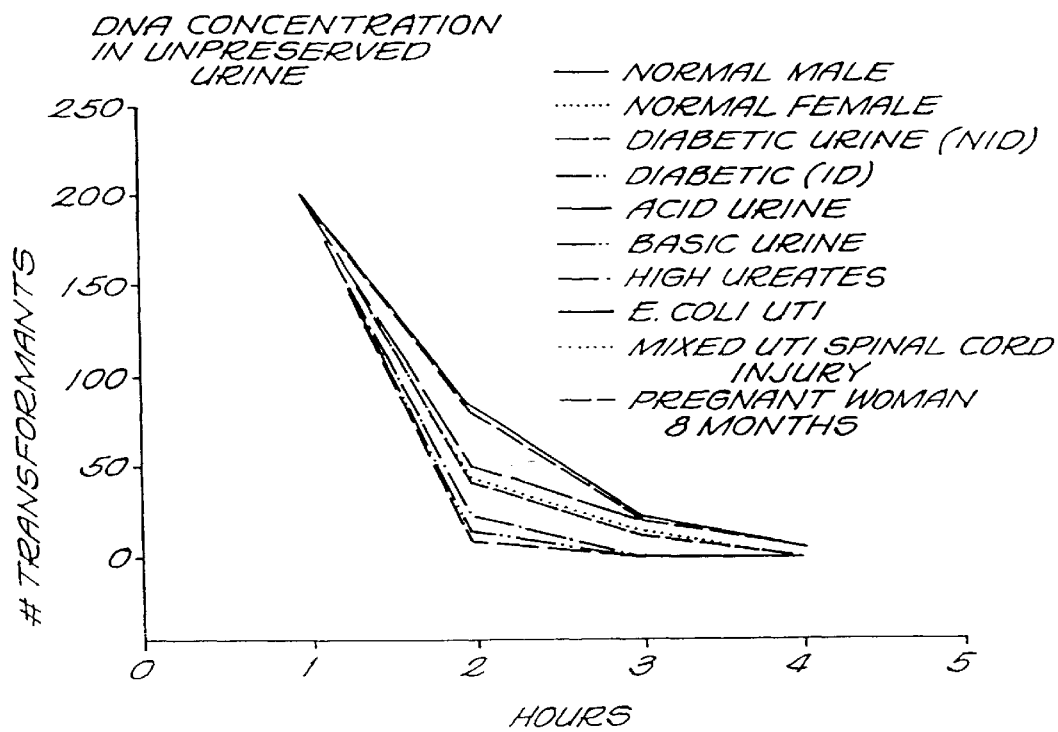
FIG. 1 is a graph of DNA concentration in unpreserved urine according to the prior art.
Figure 2:
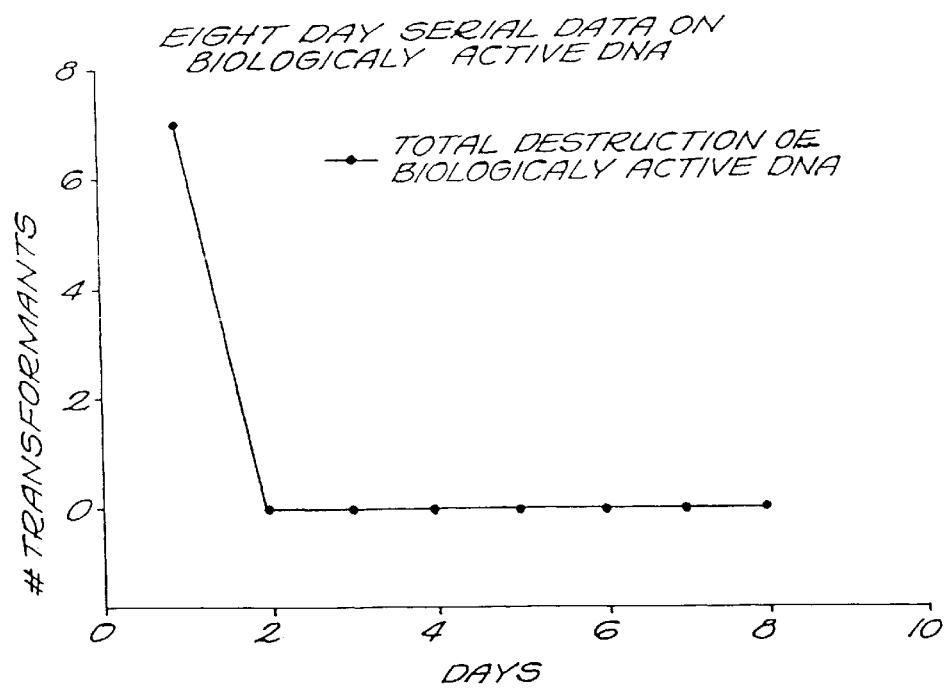
FIG. 2 is a graph of eight day serial data on unpreserved urine according to the prior art.
Figure 3:
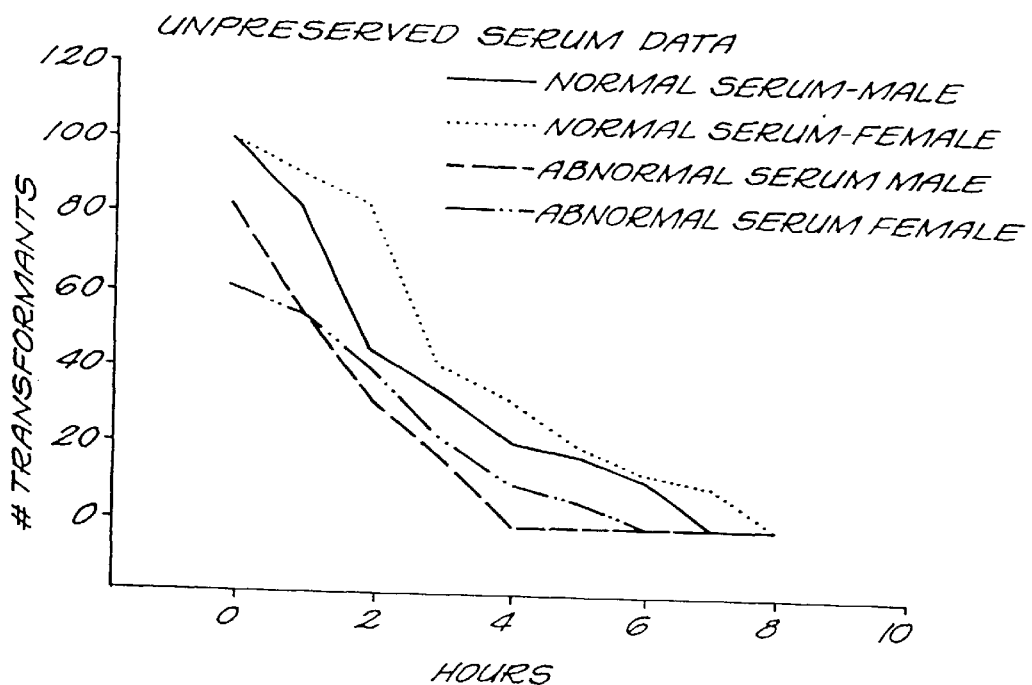
FIG. 3 is a graph of DNA concentration in unpreserved serum according to the prior
Figure 4:
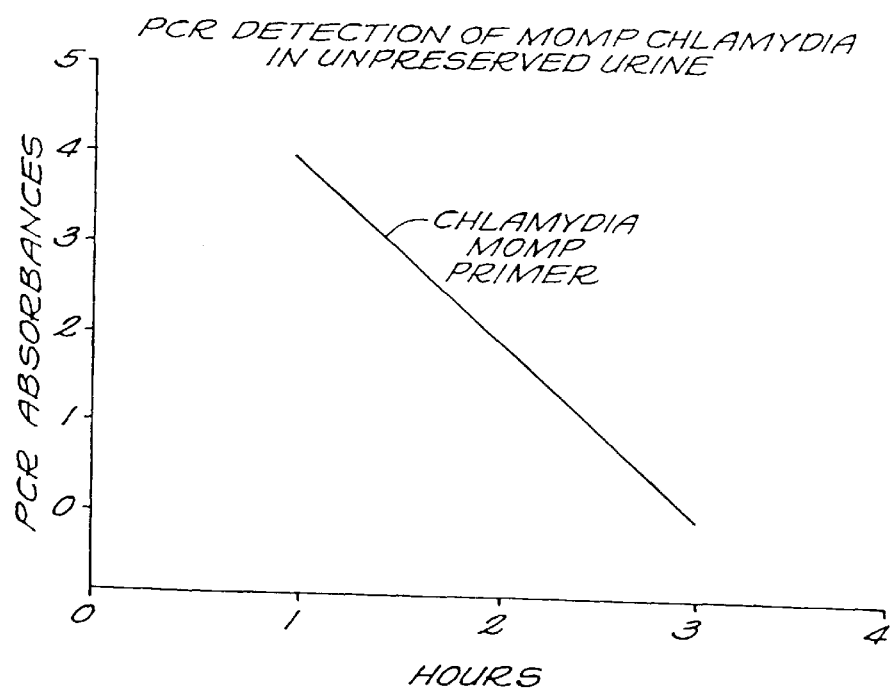
FIG. 4 is a graph of PCR detection of MOMP Chlamydia in unpreserved urine according to the prior art.

Improved methods, systems and reagents for preserving nucleic acids, e.g., DNA and RNA, in bodily fluids are disclosed herein. In one advantageous embodiment, the invention is may be used for preservation of nucleic acids in urine. In another advantageous embodiment, the invention enables the molecular assay of nucleic acids in other bodily fluids and excretions, such as blood, blood serum, amniotic fluid, spinal fluid, conjunctival fluid, salivary fluid, vaginal fluid, stool, seminal fluid, and sweat to be carried out with greater sensitivity, as the methods and preservatives of the invention have been found to surprisingly increase the signal obtained with such nucleic acid testing methods as the polymerase chain reaction (PCR), $LC_x$, and genetic transformation testing (GTT). In particular, the invention has also been found to surprisingly modulate the effect of hemoglobin, e.g., methemoglobin, interference on nucleic acid assays such as PCR on serum samples. Additionally, hybridization in such nucleic acid testing methods is unexpectedly improved.

In an embodiment, the invention relates to methods of preserving a nucleic acid in a fluid such as a bodily fluid, including providing a nucleic acid preservative solution comprising an amount of a divalent metal chelator selected from ethylenediaminetetraacetic acid (EDTA), [ethylenebis(oxyethylenenitrilo)]tetraacetic acid (EGTA) and 1,2-bis(2-aminophenoxy)ethane-N,N,N',N'-tetraacetic acid (BAPTA), or salts thereof; and an amount of at least one chelator enhancing component selected from lithium chloride, guanidine, sodium salicylate, sodium perchlorate, and sodium thiocyanate; and adding the nucleic acid preservative to the fluid, e.g., a bodily fluid. The amount of the divalent metal chelator is generally in the range of from about 0.001M to 0.1M, and the amount of the chelator enhancing component is generally in the range of from about 0.1M to 2M. The amount of chelator enhancing component is more desirably at least 1M in the preservative solution, and the divalent metal chelator is desirably present in an amount of at least about 0.01M.

In another embodiment, the invention relates to nucleic acid preservative solutions comprising an amount of a divalent metal chelator selected from EDTA, EGTA and BAPTA, and salts thereof; and an amount of at least one chelator enhancing component selected from lithium chloride, guanidine, sodium salicylate, sodium perchlorate, and sodium thiocyanate. The amount of the divalent metal chelator is generally in the range of from about 0.001M to 0.1M, and the amount of the chelator enhancing component is generally in the range of from about 0.1M to 2M. The amount of chelator enhancing component is more desirably at least 1M in the preservative solution, and the divalent metal chelator is desirably present in an amount of at least about 0.01M.

The methods and preservatives of the invention may further include an amount of at least one enzyme inactivating component such as manganese chloride, sarkosyl, or sodium dodecyl sulfate, generally in the range of about 0–5% molar concentration.

In yet another aspect the invention relates to a method of improving the signal response of a molecular assay of a test sample, including providing a nucleic acid preservative solution comprising an amount of a divalent metal chelator selected from EDTA, EGTA and BAPTA, and salts thereof; and an amount of at least one chelator enhancing component selected from lithium chloride, guanidine, sodium salicylate, sodium perchlorate, and sodium thiocyanate; adding the nucleic acid preservative to a test sample to provide a preserved test sample; extracting molecular analytes of interest, e.g., DNA, from the preserved test sample, and conducting a molecular assay on the extracted molecular analytes of interest. The amount of the divalent metal chelator is generally in the range of from about 0.001M to 0.1M, and the amount of the chelator enhancing component is generally in the range of from about 0.1M to 2M. The chelator enhancing component is more advantageously one or more of sodium perchlorate, sodium thiocyanate, sodium perchlorate, guanidine, and lithium chloride. The amount of chelator enhancing component is more desirably at least 1M in the preservative solution, and the divalent metal chelator is desirably present in an amount of at least about 0.01M. Signal response is believed to be enhanced in part due to enhanced hybridization as a result of the use of the reagents of the present invention.

Use of the methods and preservatives disclosed herein eliminate enzymatic destruction of the nucleic acid of interest in the bodily fluid. The preservative can optionally be provided in solid or gaseous forms. While the methods and preservatives of the invention are useful in preserving all types of nucleic acids, e.g., RNA and DNA, including human DNA, and bacterial, fungal, and viral DNA, the invention is especially advantageous for use in preserving prokaryotic DNA, e.g., gonococcal DNA, DNA of *Haemophilus influenzoe* and *Bacillus subtilis*. Nucleic acids in a bodily fluid are preserved for testing for a significantly longer period of time than that permitted by the prior art. While the maximum time between collecting, mailing, and testing patient specimens is expected to be approximately six days, the invention is effective beyond that period of time.

The preservatives of the invention may be used advantageously to preserve prokaryotic, e.g., gonococcal DNA, as shown below, although the teachings of the invention may be readily applied to the preservation of other types of DNA, including human, bacterial, fungal, and viral DNA, as well as to RNA. The reagents of the invention are believed to function by inactivating two classes of enzymes present in bodily fluids such as blood or urine which the inventor has recognized as destructive to DNA integrity, metal-dependent and metal independent enzymes. The divalent metal chelator removes, e.g., magnesium and calcium cation ($Mg^{+2}$, $Ca^{+2}$) so as to effectively inactivate metal dependent enzymes such as deoxyribonucleases, a component of which has been found to inactivate gonococcal DNA in unpreserved urine. The divalent metal chelator may be ethylenediaminetetraacetic acid (EDTA), [ethylenebis(oxyethylenenitrilo)]tetraacetic acid (EGTA), or 1,2-bis(2-aminophenoxy)ethane-N,N,N',N'-tetraacetic acid (BAPTA), or salts thereof. The amount of the divalent metal chelator is generally in the range of from about 0.001M to 0.1M. More desirably, the amount of the divalent metal chelator in the preservative solution is at least 0.01M.

The second component of the reagents disclosed herein include a chelator enhancing component which assists the divalent metal chelator in protecting the nucleic acids in the fluid. These chelator enhancing components are believed to inactivate metal independent enzymes found in bodily fluids such as DNA ligases, e.g., D4 DNA ligase; DNA polymerases, e.g., T7 DNA polymerase; exonucleases, e.g., exonuclease 2, λ-exonuclease; kinases, e.g., T4 polynucleotide kinase; phosphotases, e.g., BAP and CIP phosphotase; nucleases, e.g., BL31 nuclease, and XO nuclease; and RNA-modifying enzvmes such as *E coli* RNA polymerase, SP6, T7, T3 RNA polymerase, and T4 RNA ligase. Lithium chloride, guanidine, sodium salicylate, sodium perchlorate, and sodium thiocyanate have been found to be particularly effective. The amount of the chelator enhancing component is generally in the range of from about 0.1M to 2M, and more desirably the amount of chelator enhancing component in the preservative solution is at least 1M.

Figure 12:
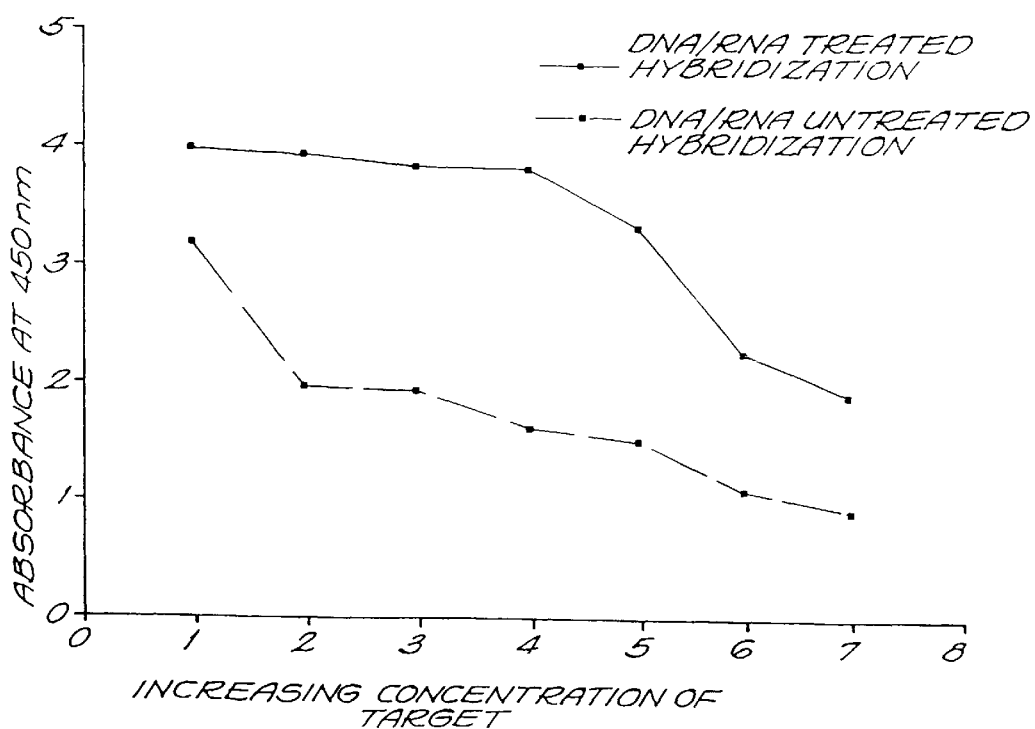
FIG. 12 graphically illustrates a comparison of signal response in PCR assays wherein the DNA has been treated with a preservative of the invention, and one which has not.

The methods and preservatives of the invention have been found to surprisingly increase the signal obtained with such nucleic acid testing methods as the polymerase chain reaction (PCR), $LC_X$, and genetic transformation testing (GTT). The invention has been found to surprisingly and unexpectedly enhance hybridization in such nucleic acid testing methods such as the PCR. FIG. 12 illustrates the improvement in hybridization obtained by use of a preservative disclosed herein on the hybridization of penicillinase-producing *Neisseria gonorrhea* (PPNG) DNA and PPNG-C probe.

A further aspect of the invention relates to methods of improving hybridization of nucleic acids, including contacting a test nucleic acid with a nucleic acid preservative solution comprising an amount of a divalent metal chelator selected from ethylenediaminetetraacetic acid (EDTA), ethylenebis(oxyethylenenitrilo)]tetraacetic acid (EGTA) and 1,2-bis(2-aminophenoxy)ethane-N,N,N',N'-tetraacetic acid (BAPTA), or salts thereof in the range of from about 0.001M to 0.1M; and an amount of at least one chelator enhancing component selected from lithium chloride, guanidine, sodium salicylate, sodium perchlorate, and sodium thiocyanate in the range of from about 0.1M to 2M, such that a test solution is formed; and contacting the test solution with a target nucleic acid under conditions favorable for hybridization, such that hybridization occurs.

Figure 13:
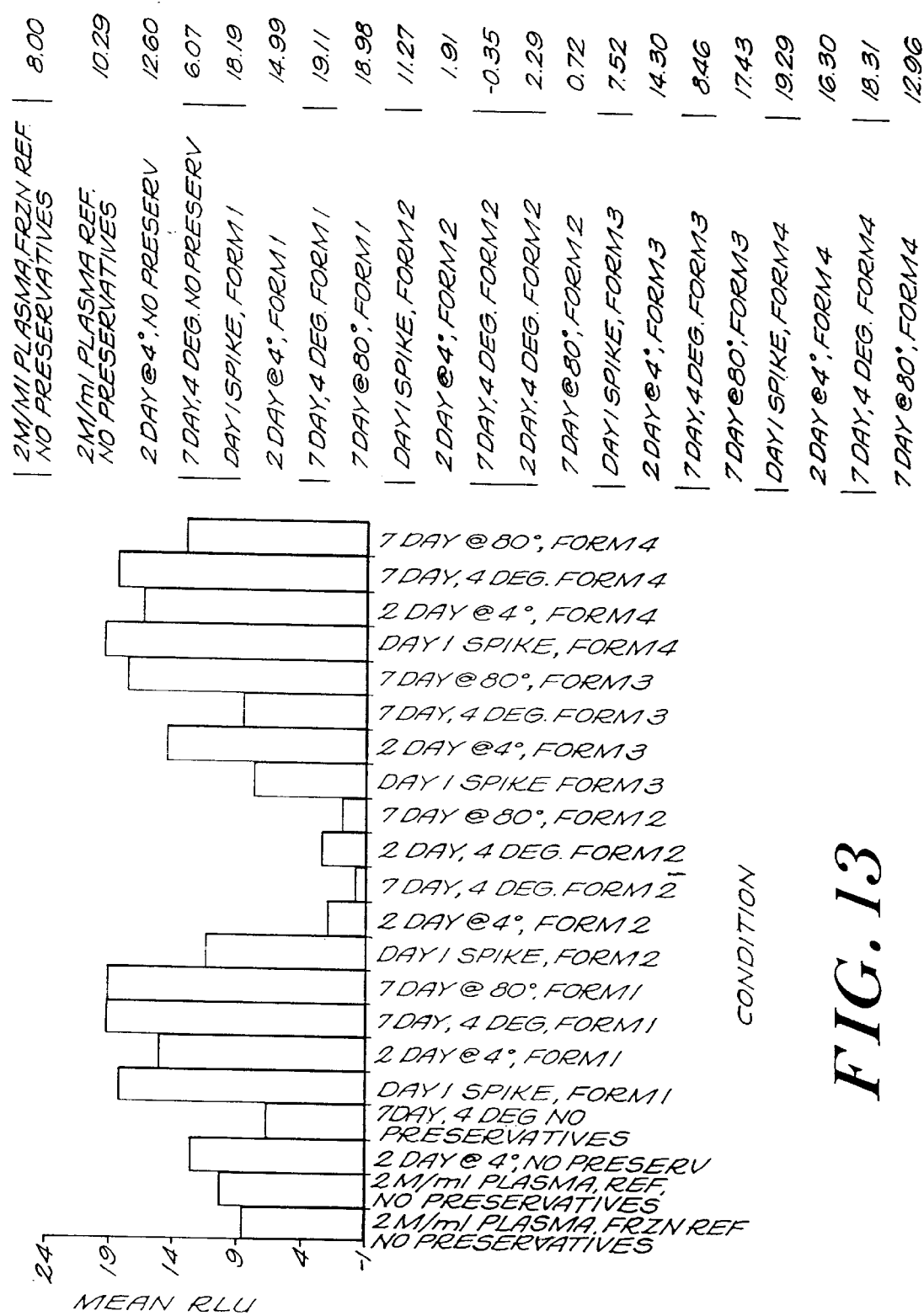
FIG. 13 illustrates the efficacy of reagents of the present invention to enhance signal response of a branched DNA assay of blood plasma samples subjected to various storage conditions.
Figure 14:
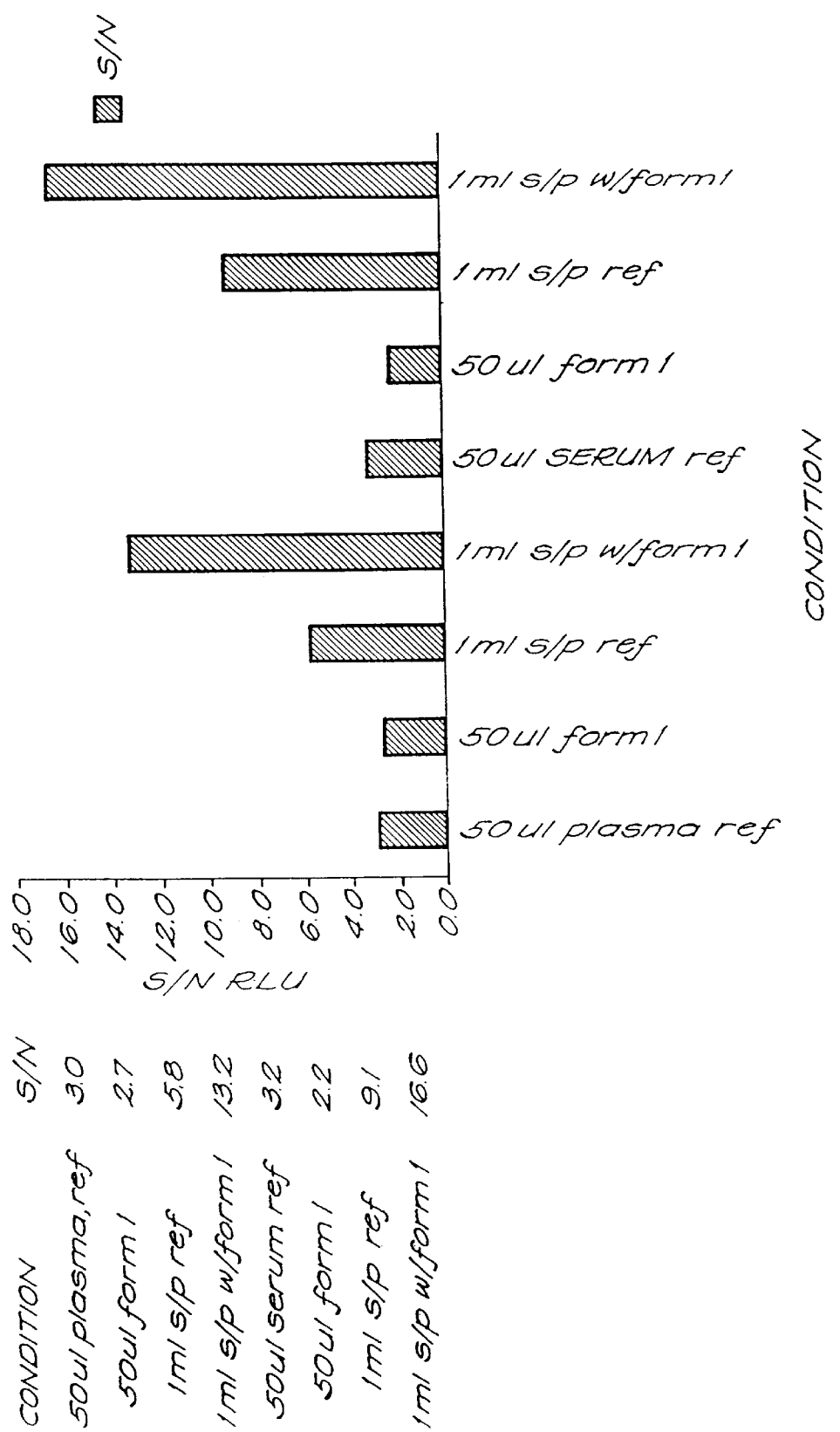
FIG. 14 illustrates the efficacy of reagents of the present invention to enhance signal response of a branched DNA assay of blood serum and plasma samples.

FIGS. 13 and 14 further illustrate the efficacy of the methods and preservatives of the invention in improving the results obtained with nucleic acid testing methods, in this case, a branched DNA assay (Chiron). In the tests run in FIG. 13, the bDNA assay was used to assess the protective effect of the DNA/RNA protect reagents. DNA sequences from the hepatitis C virus were spiked into serum and plasma. The protected serum and plasma were mixed with 9 ml of serum or plasma and 1 ml of preservative. The following formulations were used: 1) 1M guanidine HCL/ 0.01M EDTA, 2) 1M sodium perchlorate/0.01M BAPTA, 3) 1M sodium thiocyanate/0.01M EGTA, and 4) 1M lithium chloride/0.01M EGTA. The formulations were stored for seven days at 4° C. bDNA assay relies on hybridization; it can clearly be seen from the absorbance results that the target sequences were not only protected against degradation, but the more than doubling of the absorbance results indicates an enhancement of hybridization/annealing of the target sequences.

FIG. 14 illustrates a serum v. plasma study. 50 μl samples of fresh human plasma, and 1ml samples of fresh human serum were protected with 1M guanidine HC/0.01M EDTA and the bDNA assay was run on these samples after the samples were stored at 20° F. for 48 hours. Results were compared to unprotected samples. It can clearly be seen from the absorbance results that the target sequences were not only protected against degradation, but the more than doubling of the absorbance results indicates an enhancement of hybridization/annealing of the target sequences.

Figure 15:
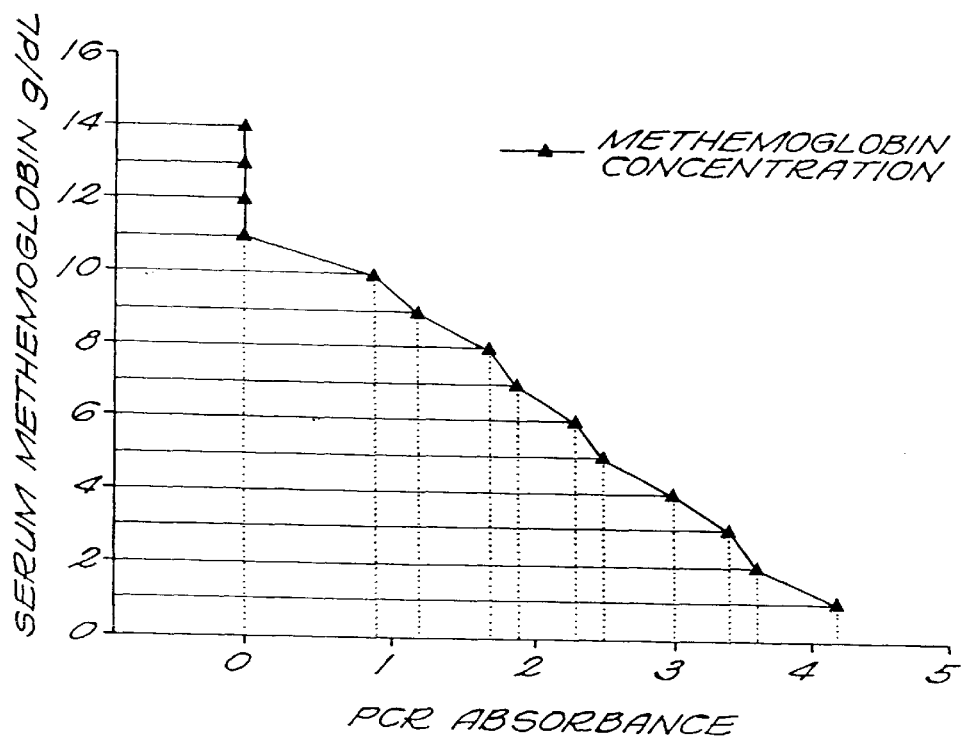
FIG. 15 is a graph showing the interference of methemoglobin on PCR absorbance in a PCR amplification assay on hepatitis B sequences MD03/06 in unprotected serum.
Figure 16:
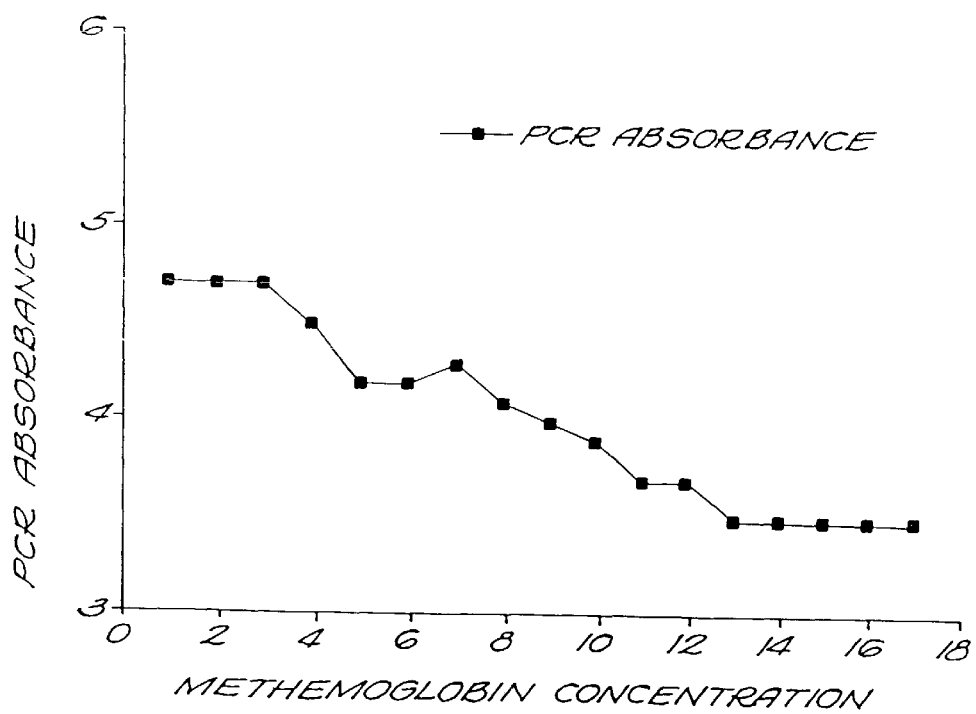
FIG. 16 is a graph showing the improvement in attenuating the interference of methemoglobin on PCR absorbance in a PCR amplification assay on hepatitis B sequences MD03/06 in serum which has been treated with a preservative of the invention.

The preservative reagents of the invention have also surprisingly been found to remove the interference with heme compounds, e.g., methemoglobin, on PCR assays run on blood serum. FIGS. 15 and 16 illustrate the improvement obtained by use of the preservatives disclosed herein. Increasing amounts of methemoglobin were spiked into unprotected fresh human serum, to a concentration of 10 dl/ml. Serial PCR assays were run over a four hour period.

Figure 17:
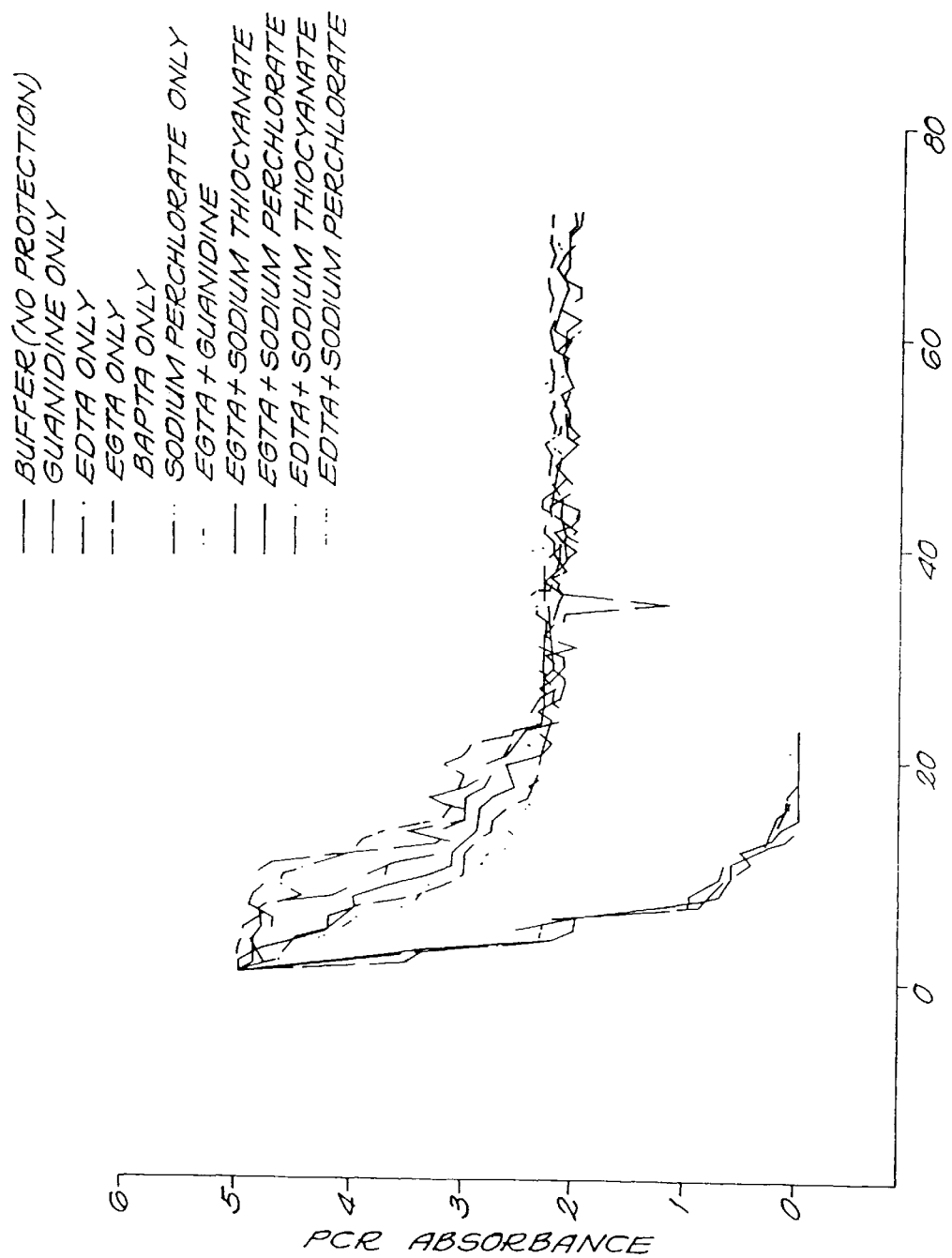
FIG. 17 illustrates the synergistic effect provided by the components of the inventive reagents in protecting hepatitis B sequences in serum stored at room temperature and subsequently subjected to MD03/06 PCR detection.
Figure 18A:
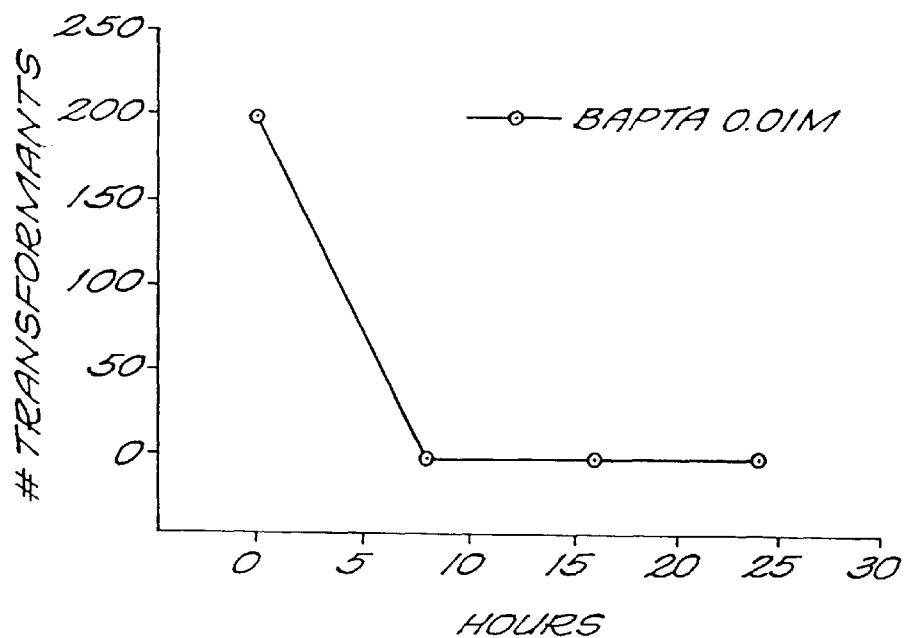
FIGS. 18A–18G are graphs showing the absence of preservative effect on gonococcal DNA in urine stored at room temperature and subsequently subjected to PCR detection offered by the individual addition of certain components which are included in the reagents of the invention.
Figure 18B:
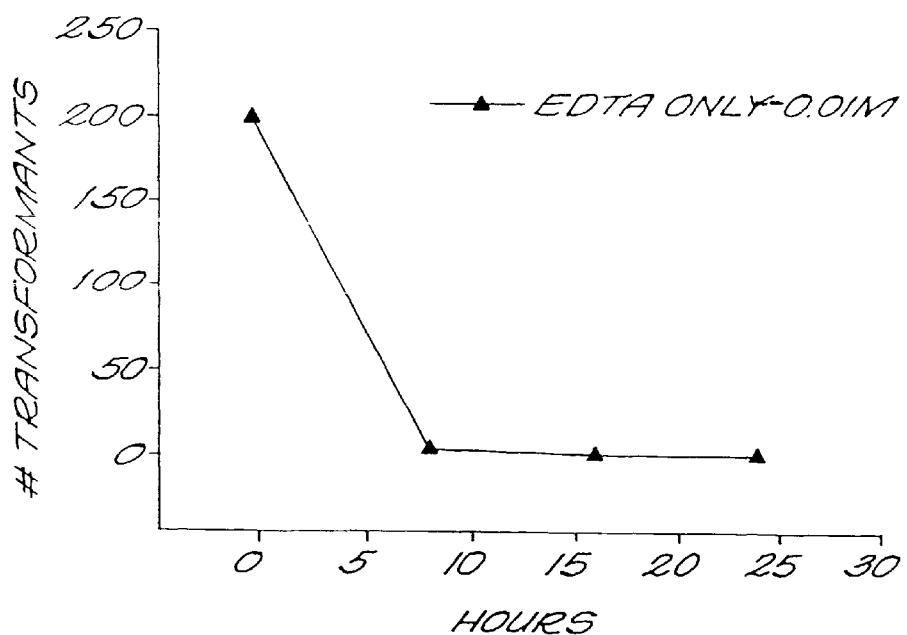
Figure 18C:
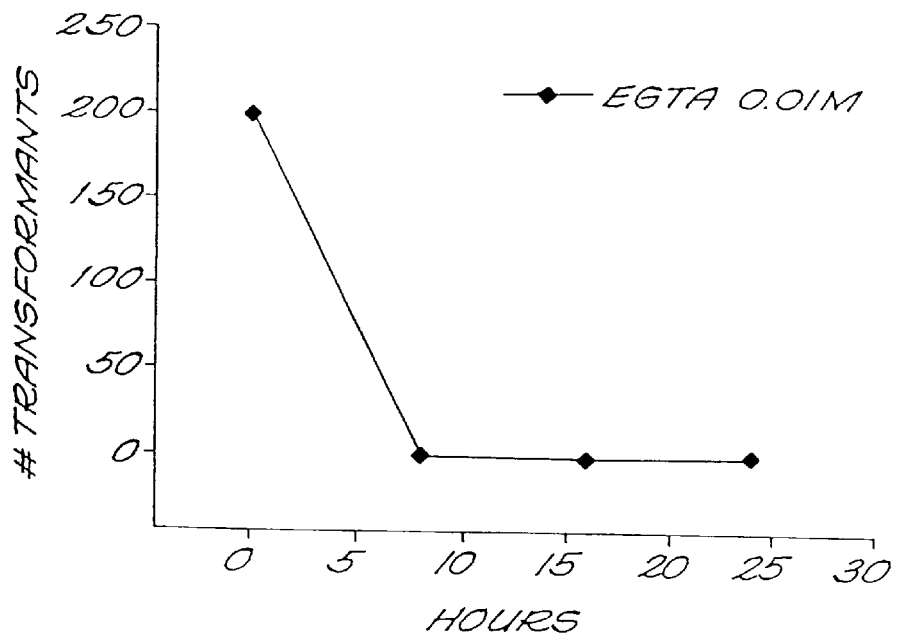
Figure 18D:
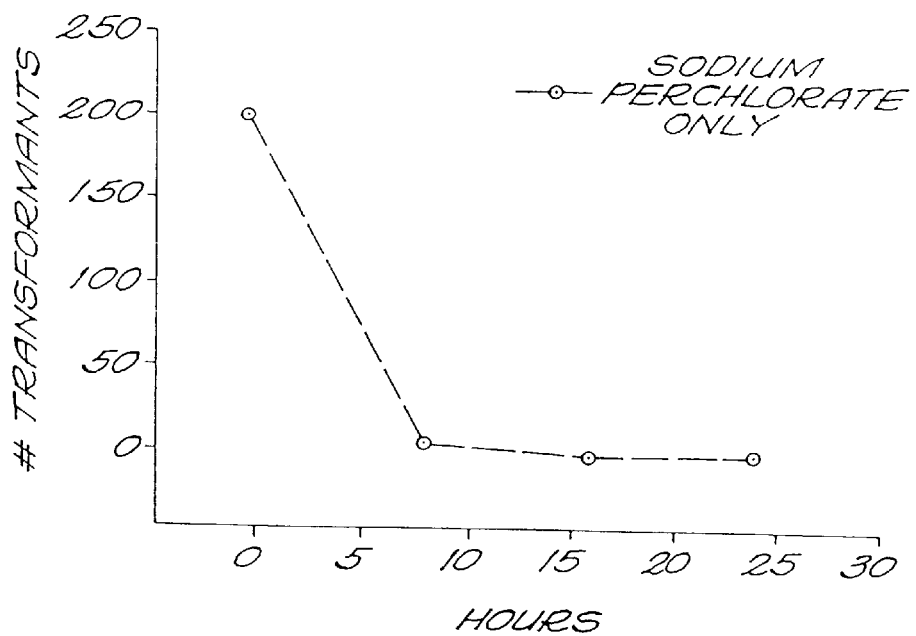
Figure 18E:
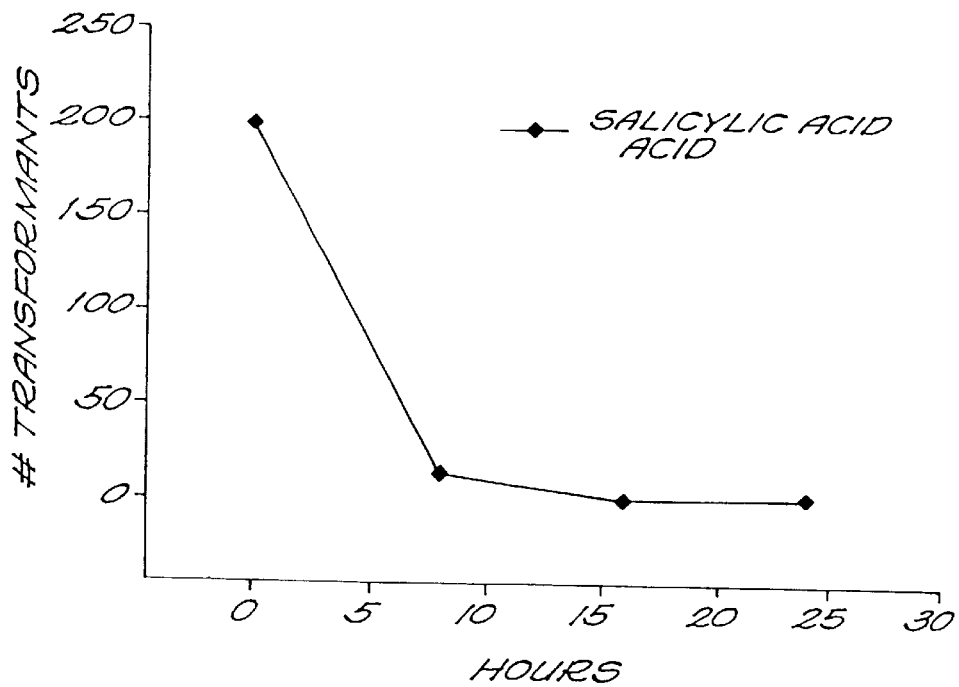
Figure 18F:
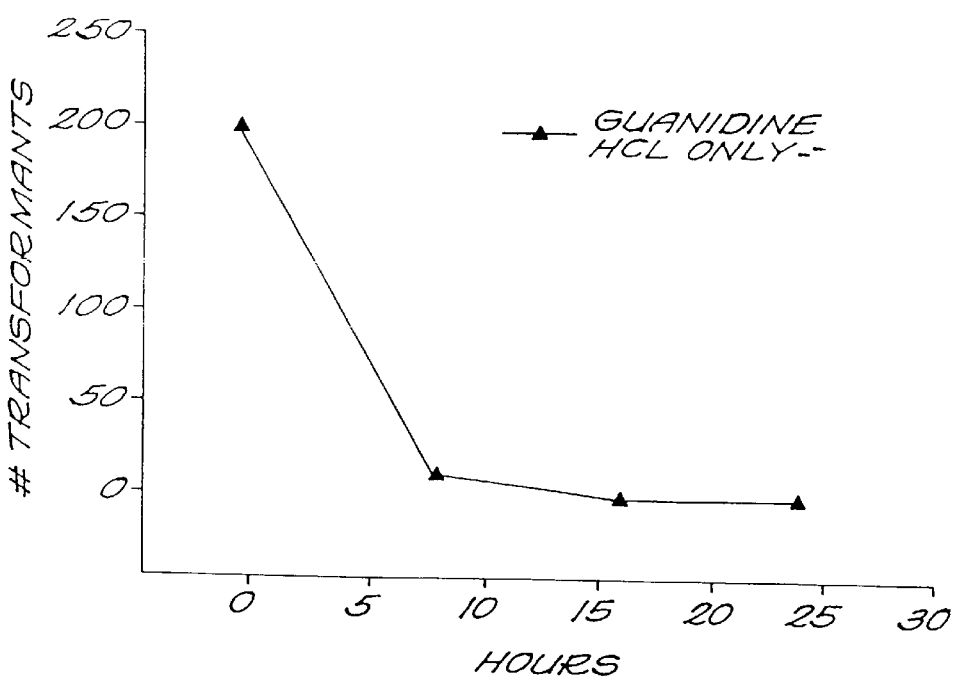
Figure 18G:
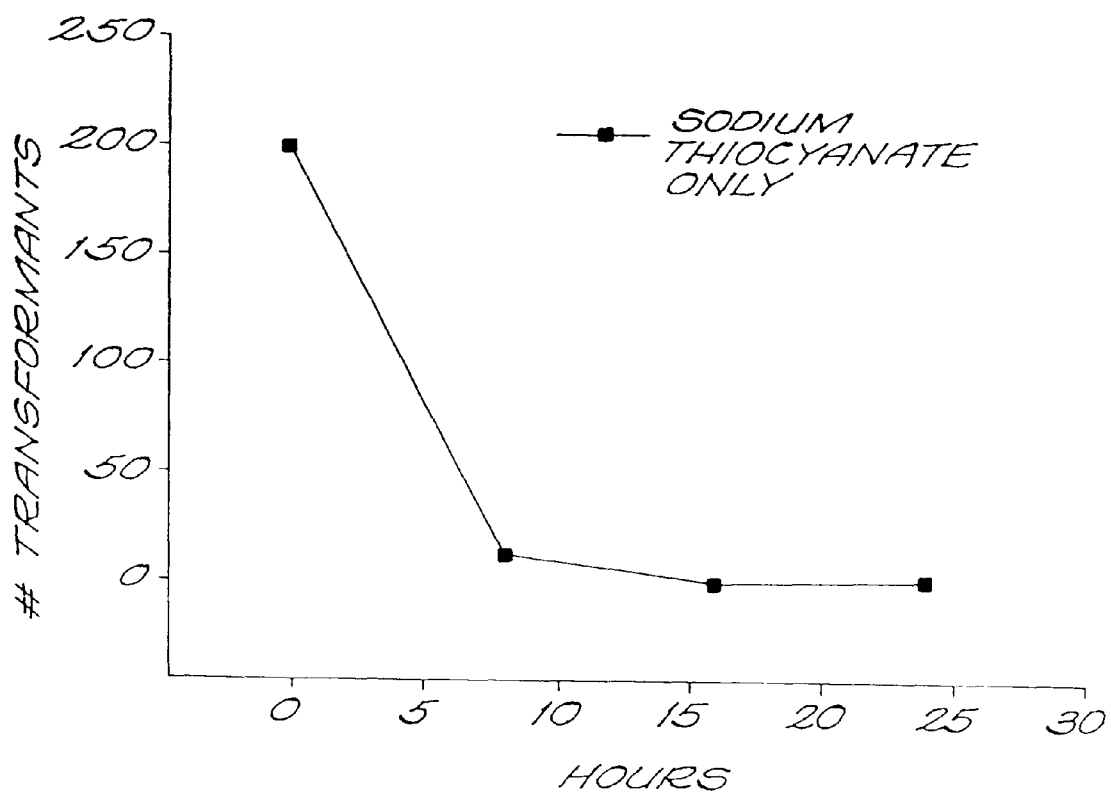

FIG. 17 illustrates the surprising and synergistic effect obtained by the combination of divalent metal chelators and chelator enhancing components in the inventive reagent (i.e., 1M sodium perchlorate/0.01M EGTA) in protecting hepatitis B sequences in serum stored at room temperature and subsequently subjected to MD03/06 PCR detection. The protocol run was as above (i.e., as illustrated in FIG. 16.) It can be seen from the figures that compared to the addition of EGTA or sodium perchlorate individually, but protection of Hep B sequences is dramatically increased when preservative solutions of the present invention are used.

FIG. 18 illustrates the relatively weak preservative effect on gonococcal DNA in urine stored at room temperature and subsequently subjected to PCR detection offered by the individual addition of components of the reagents of the present invention, i.e., divalent metal chelators 0.01M BAPTA (18A), 0.01M EDTA (18B), 0.01M EGTA (18C); and chelator enhancing components 1M sodium perchlorate (18D), 1M salicylic acid (18E), 1M guanidine HCl (18F), 1M sodium thiocyanate (18G), and lithium chloride (18H). The number of transformants in ten types of urine specimens were tested using a GTT, counted hourly, and then summarized. The standard Gonostat protocol (see Example 2, infra) was employed and illustrated the synergistic effect obtained by the combination of divalent metal chelators and chelator enhancing components in protecting gonococcal DNA in urine stored at room temperature and subsequently subjected to PCR detection.

Figure 11:
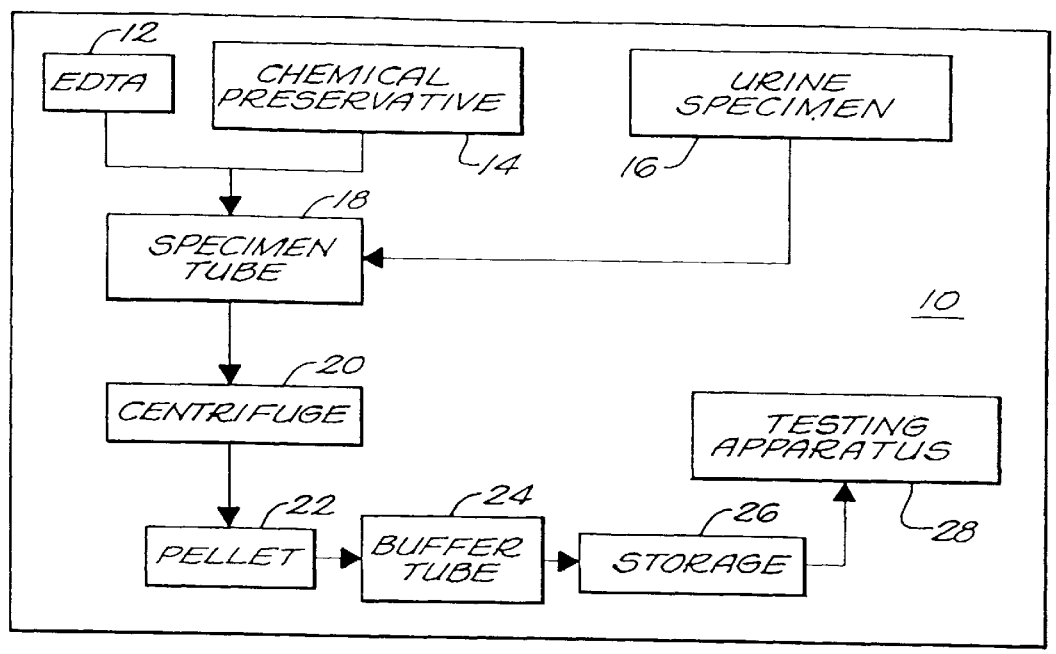
FIG. 11 is a diagram of the system for preserving DNA according to one embodiment of the invention.

Another embodiment of the invention, a method 10 for preserving DNA, is illustrated diagrammatically in FIG. 11. This embodiment uses an exemplary protocol to preserve and test the urine specimens. The protocol is described in Table 1, below. This system produces high yields of DNA/ RNA suitable for such testing methods as PCR, restriction fragment length polymorphisms assay (RFLP), and nucleic acid probes from urine specimens.

Table 1

1. 10 ml of clean catch urine 16 is added to a specimen test tube 18 containing divalent metal chelator 12 and chelator enhancing component 14. Test tube is inverted two or three times to mix the urine.
2. Test tube is transported to laboratory. No refrigeration is necessary. Note: The test tube should be stored in a cool place and not in direct sunlight.
3. At the laboratory, the test tube is centrifuged 20 at 3200 rpm for 10 minutes.
4. Using a sterile transfer pipette, the pellet 22 at the bottom of the test tube is transferred to another test tube containing buffer 24. (As little urine as possible should be transferred with the pellet material.)
5. The buffered material is stored 26 at between 2–8° C. until ready to test 28.
6. The specimen size necessary to run the assay-needs to be validated on the individual test methodology and individual testing protocol being used.

A test kit embodiment can advantageously be provided. For example, a specimen test tube containing the preservative reagent of the invention and a buffer test tube can be provided together for laboratory use. Alternatively, the specimen test tube containing the preservative reagent of the invention can be provided to an individual patient with instructions for use. The individual can then mail or bring the preserved sample to a laboratory for testing.

Other aspects of the invention are further demonstrated and illuminated by reference to the following examples, which are intended to be non-limiting.

EXAMPLE 1

Figure 5:
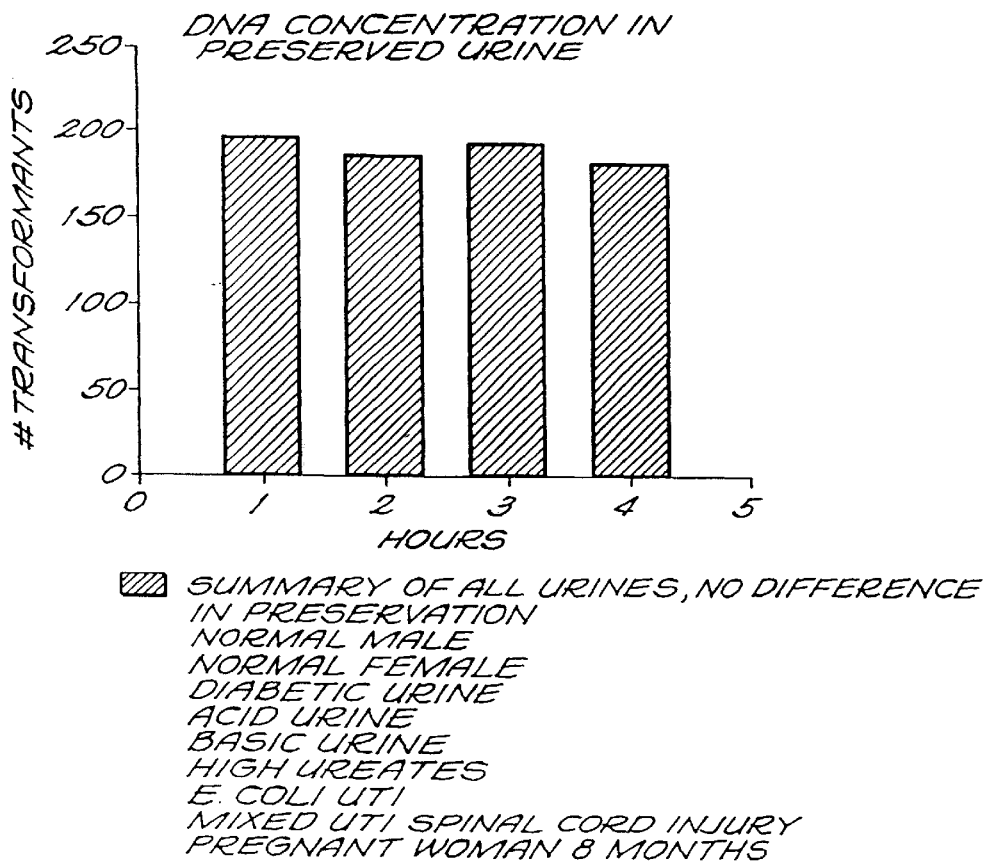
FIG. 5 is a bar graph of DNA concentration in preserved urine according to the invention.

FIG. 5 is a bar graph of DNA concentration in preserved urine in accordance with the invention. The number of transformants in ten types of urine specimens were tested using a GTT, counted hourly, and then summarized. The standard Gonostat protocol (see Example 2, infra) was employed, and the preservative used was 1M guanidine HCl/0.01M EDTA. A count of two hundred colonies demonstrates total preservation of a specimen. The number of gonococcal transformants in the preserved urine remained relatively constant approaching two hundred, throughout the four hours of the test. No significant difference in level of preservation was observed among the different types of urine specimens. Therefore, it can be seen that the invention provides nearly total protection for DNA in urine.

EXAMPLE 2

Figure 6:
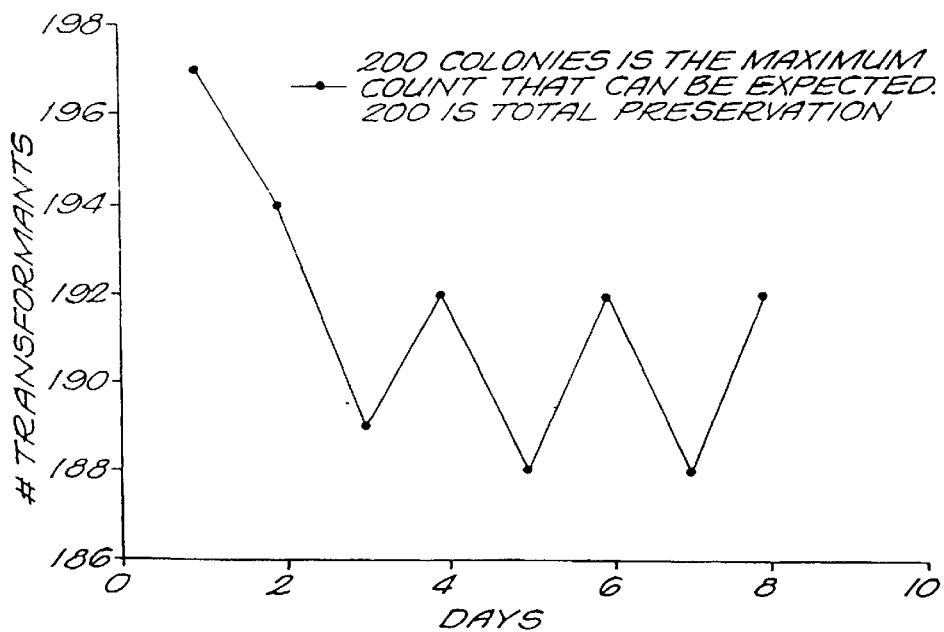
FIG. 6 is a graph of eight day serial data on preserved urine according to the invention.

FIG. 6 is a graph of eight day GTT serial data on preserved urine according to the invention. 1 pg of gonococcal DNA was spiked into 9 ml of fresh human urine and 1 ml of aqueous preservative containing 1M sodium perchlorate and 0.01M EGTA. 300 µl was spotted onto a lawn of the Gonostat organism at 24 hour intervals for eight days. The plates contained BBL Chocolate II agar and were incubated at 37° C. for 24 hours before readings were taken. The number of colonies observed throughout the eight-day testing period ranged from a low count of one hundred eighty-eight to a high count of one hundred ninety-seven. Thus, it can be seen that the invention preserves DNA in urine for a significantly longer period of time than previously provided.

EXAMPLE 3

Figure 7:
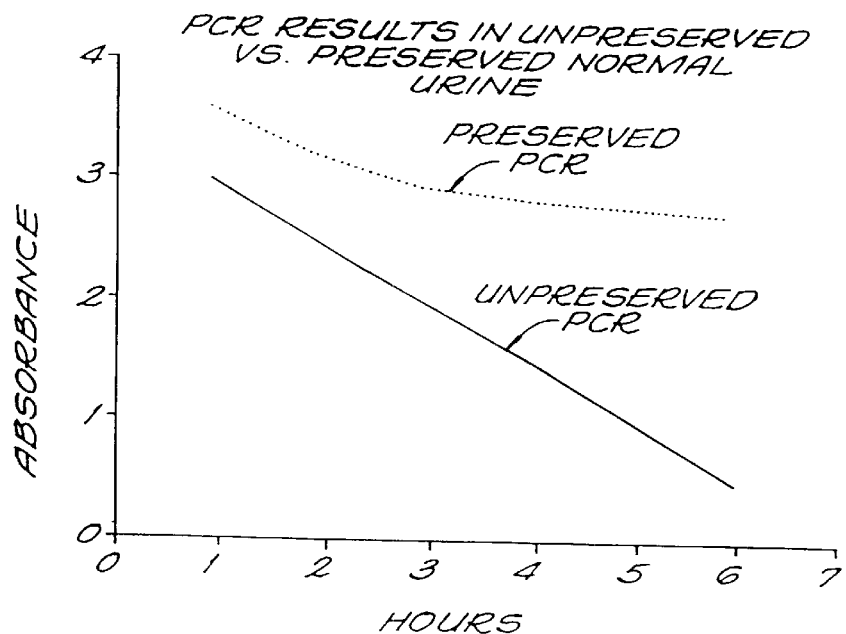
FIG. 7 is a graph comparing PCR results in unpreserved and preserved normal urine according to the invention.

FIG. 7 is a graph comparing PCR results in unpreserved and preserved normal urine according to the invention. A MOMP template to *Chlamydia trachomatis* was used and amplified using a standard PCR protocol. 200 copies of the MOMP target were spiked into 9 ml of fresh human urine containing 1M sodium perchlorate and 0.01M BAPTA. PCR was done each hour for eight hours total. In the unprotected urine, approximately three PCR absorbances were measured one hour after the addition of DNA to the urine. The number of PCR absorbances approached zero by the sixth hour. By contrast, in the preserved specimen, in excess of three PCR absorbances were measured at the one hour testing. However, approximately three PCR absorbances were still observed by the sixth hour. Therefore, the invention preserves sufficient DNA and nucleic acid sequences to permit PCR testing well beyond the testing limits of unpreserved urine. The results shown in the Figure are consistent for all types of DNA in a urine specimen.

EXAMPLE 4

Figure 8:
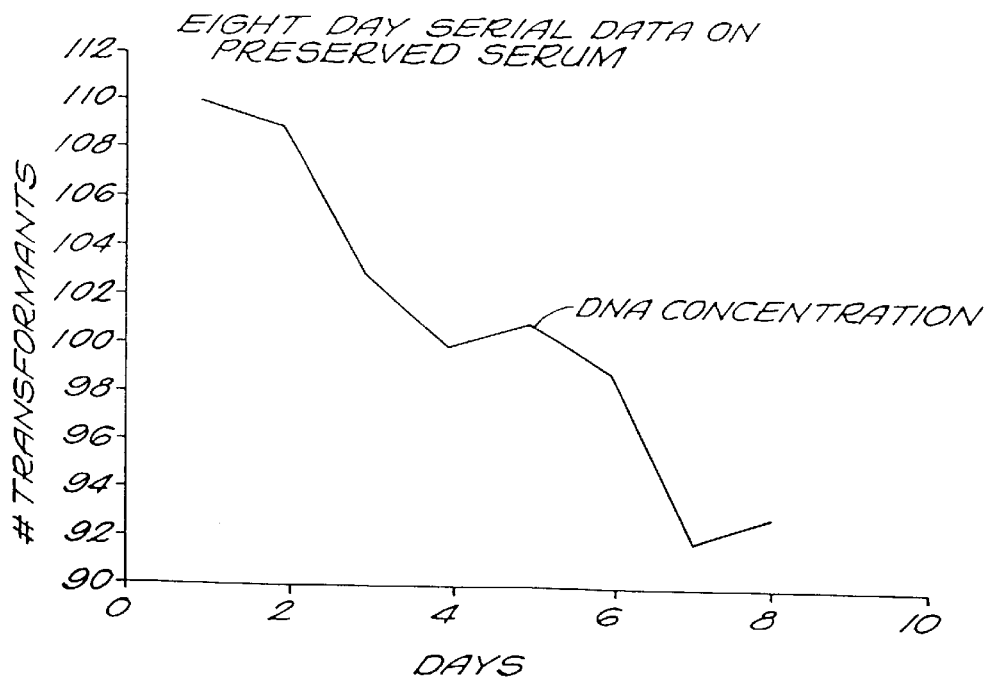
FIG. 8 is a graph of eight day serial data on preserved serum according to the invention.

The reagents and methods of the invention may be used for preserving other bodily fluids and excretions, such as blood serum. FIG. 8 is a graph of eight day serial data on preserved serum according to the invention. The protocol used was similar to Example 3, except fresh human serum was used. The number of transformant colonies observed throughout the eight-day testing period ranged from a high count of one hundred ten at the one day measurement to a low count of approximately ninety-two at the seven day measurement. In fact, the test results actually showed an increase in transformant colonies between days seven and eight. Thus, it can be seen that the invention preserves DNA in serum for a significantly longer period of time than previously attainable.

EXAMPLE 5

Figure 9:
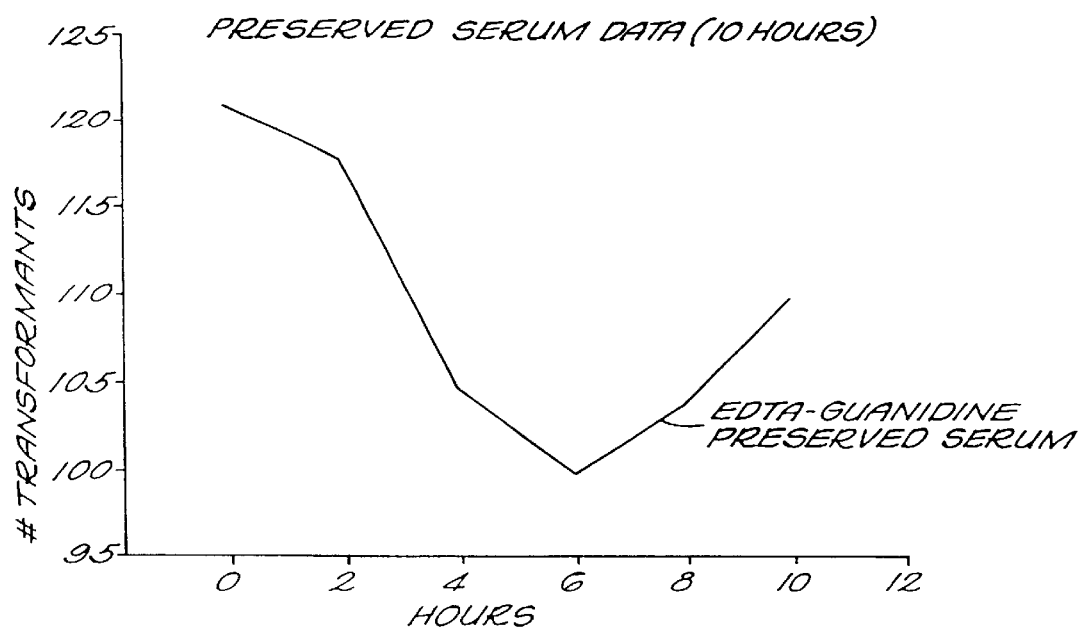
FIG. 9 is a graph of DNA concentration in preserved serum according to the invention.
Figure 10:
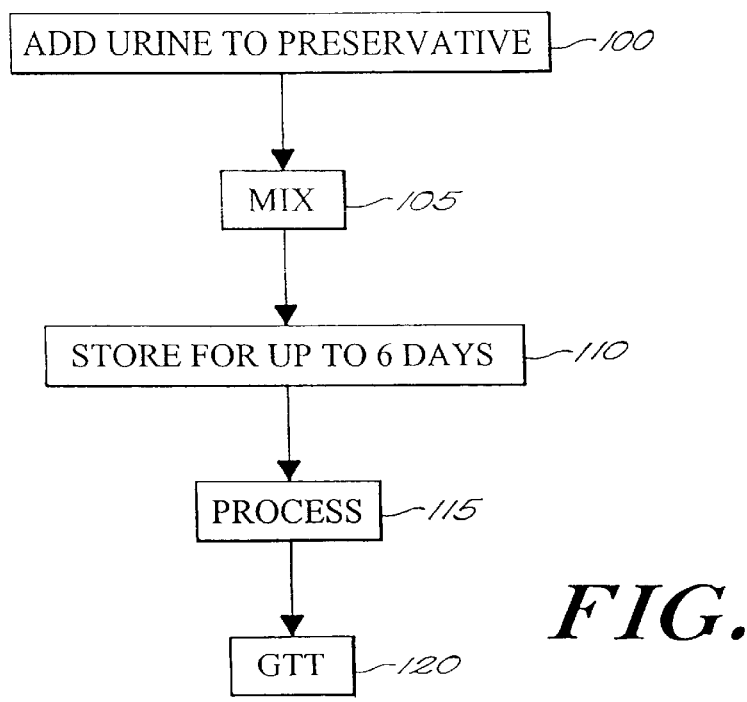
FIG. 10 is a flow chart of the method for preserving DNA according to one embodiment of the invention.

FIG. 9 is a graph of DNA concentration in preserved serum according to the invention. The serum was preserved with preservative solution comprising 1M guanidine HCV/0.01M EDTA. The protocol used was similar to Example 3, except fresh human serum was used, and the duration time of the study was ten hours. In excess of 120 transformants were measured at the time gonococcal DNA was added to the serum. Approximately 100 transformants were counted at the six hour measurement. However, by the tenth hour, testing indicated that the concentration of biologically active DNA in the preserved serum had increased to approximately 110 transformant colonies.

EXAMPLE 6
Preservation of DNA in Simulated Clinical Specimens

In the following experiment, simulated clinical urine specimens were produced and tested for the presence of gonococcal DNA. The chemicals listed in Table 2, below, were added, at the concentrations previously described, to urine specimens from healthy adults, as was EDTA.

A suspension of gonococci was immediately added to each urine specimen. The added gonococci were an ordinary strain of *N. Gonorrhoeae*, 49191, which was grown overnight on GC agar medium at 37° C. in a 5% $CO_2$ atmosphere. The *N. Gonorrhoeae* colonies were picked and suspended in GC buffer. A 1/10 volume of a suspension containing approximately 10 Colony forming units (cfu) per ml was added to the urine. As a positive control, the suspension of gonococci was also added to Hepes buffer.

All simulated clinical specimens and the Hepes controls were tested at time zero, i.e., when the chemicals and gonococci were added. The specimens and controls were also tested after storage at room temperature for six days. This six day period was selected to approximate the maximum time expected between collecting, mailing, and testing patient specimens.

With the exception of urine samples containing SDS and sarkosyl, the simulated specimens and Hepes controls were processed as follows:

1. A 10 ml quantity was centrifuged at 4000 rpm for 30 minutes.
2. The supernatant was decanted, and the pellet was suspended in 1ml $PO_4$ buffer.
3. The suspension was heated for 10 minutes in a water bath at 60° C.
4. After cooling, the suspension was used in the GTT.

The simulated urine specimens containing SDS-EDTA or sarkosyl-EDTA were processed as follows:

1. Approximately a 2½ volume (approximately 25 ml) of 95% ethyl alcohol was added to the tube with the urine and preservative. The contents were mixed by inverting the tube several times.
2. The mixture was centrifuged at 4000 rpm for 30 minutes.
3. The pellet was suspended in 10 ml of 70% alcohol and centrifuged.
4. The pellet was then suspended in 1 ml $PO_4$ buffer.
5. The suspension was heated for 10 minutes in a water bath at 60° C.
6. After cooling, the suspension was used in the GTT.

The inoculated urine was stored at room temperature for 6 days prior to testing. The formulations that preserved (+) or did not preserve (−) gonococcal DNA in the inoculated urine for six days to approximately the same degree as in the Hepes buffer control are indicated. Although the results of the Gonostat® assay can be semi-quantitated, the tests were not designed to rank the relative efficacy of the chemical preservatives. Thus, the results given in Table 2 indicate whether or not the particular chemical preserved DNA in urine over a six day period to same degree as in the Hepes buffer.

TABLE 2

| Preservative | |
|---|---|
| + | − |
| 0.01M EDTA + Guanidine hydrochloride (1M) | Sodium periodate (1M) |
| 0.01M EDTA + Guanidine thiocyanate (1M) | Trichloroacetic acid (1M) |
| 0.01M EDTA + Lithium chloride (1M) | Urea (1M) |

TABLE 2-continued

| Preservative | |
|---|---|
| + | − |

0.01M EDTA + Manganese chloride (1M)
0.01M EDTA + Sarkosyl (1%)
0.01M EDTA + Sodium dodecyl sulfate (SDS) (1%)
0.01M EDTA + Sodium perchlorate (1M)
0.01M EDTA + Sodium salicylate (1M)
0.01M EDTA + Sodium thiocyanate (1M)

The 92% sensitivity exhibited with male urine specimens is comparable to the culture results reported in the literature. In addition, the 88% sensitivity exhibited with female urine specimens exceeds the previously-reported levels.

While a preferred embodiment of the invention is directed to the preservation of gonococcal DNA, it will be readily apparent to one skilled in the art that the invention is adaptable for use in preserving other types of DNA, such as that of *Haemophilus influenzae* and *Bacillus subtilis*. The invention can also be used to preserve RNA contained in bodily fluid samples. Such preserved RNA can be used for RNA transcriptase and reverse transcriptase assays for viral segments and human gene sequence testing.

Furthermore, although in the preferred embodiment the preservatives are added to a bodily fluid, e.g., a urine specimen, the urine specimen can also be added to the preservatives without detriment to the efficacy of the invention. Optimal preservation of the DNA is typically and conveniently achieved by adding a single reagent of the invention to the specimen.

EXAMPLE 7
PCR Detection of Penicillinase-producing *Neisseria gonorrhea*

The PCR signal-enhancing effect of the preservative reagents of the disclosure is demonstrated by the following example. Four varieties of TEM-encoding plasmids are found in PPNG. These are the 6.7 kb (4.4 Mda) Asian type, the 5.1 kb (3.2 Mda) African type, the 4.9 kb (3.05-Mda) Toronto type and the 4.8 kb (2.9-Mda) Rio Type. This PCR assay for PPNG takes advantage of the fact that the TEM-1 gene is located close to the end of the transposon Tn2; by the use of one primer in the TEM-1 gene and the other in a sequence beyond the end of Tn2, and common to all four plasmids, a PCR product only from plasmids and not from TEM-1 encoding plasmids was obtained. (Table 3, below) The conditions associated with this protocol were modified to include the DNA/RNA protect reagent in the hybridization and the treated probe was mixed with the 761-bp amplification product per standard PCR protocol. The results were read at $A_{450\ nm}$.

Materials and Reagents
  BBL chocolate 11 agar plates
  Sterile Tris Buffer 10 mM Tris (pH 7.4), 1 mM EDTA
  0.5-ml Gene Amp reaction tubes
  Sterile disposable pasteur pipette tips
  Aerosol-resistant tips
  PCR master mix:
    50 mM KCL
    2 mM MgCl
    50 µM each of
      Deoxyribonucleoside triphosphate;
      2.5 U of taq Polymerase (Perkin Elmer);
      5% glycerol;
      50 pmol each of primers PPNG-L and PNG-R (per 100 µl reaction)
  Denaturation solution
    1M Na 5×Denhardt's solution
  Prehybridization Solution
    5×SSC(1×SSc is 0.015 M NaCl plus 0.015 M sodium citrate);
    5×Denhardt's solution;
    0.05% SDS;
    0.1% Sodium Ppi, and
    100 µg of sonicated salmon sperm DNA per ml.
  Hybridization Solution
    Same as prehybridization solution but without Denhardt's solution and including 200 µl of DNA/RNA protect reagent 1.
  1 ml DNA/RNA preservative (1M guanidine HCl/0.01M EDTA)
  Avidin-HRP peroxidase complex (Zymed)
  Magnetic microparticles (Seradyne)

TABLE 3

| Function | Name | Nucleotide sequence 5' to 3' |
|---|---|---|
| Primer | PPNG-L | AGT TAT CTA CAC GAC GG (SEQ ID NO:1) |
| Primer | PPNG-R | GGC GTA CTA TTC ACT CT (SEQ ID NO:2) |
| Probe | PPNG-C | GCG TCA GAC CCC TAT CTA TAA ACT C (SEQ ID NO:3) |

Methods
  Sample preparation: 2 colonies were picked from a chocolate agar plate. Colonies were suspended in DI water just prior to setting up PCR. The master mix was prepared according to the recipe above. 5 µl of the freshly prepared bacterial suspension was added to 95 µl of master mix. The DNA was liberated and denatured in a thermocycler using three cycles of 3 min at 94° and 3 min at 55°. The DNA was amplified in the thermal cycler by using a two step profile: a 25 s denaturation at 95° C. and a 25 s annealing at 55° C. for a total of thirty cycles. The time was set between the two temperature plateaus to enable the fastest possible anealing between the two temperatures. 15 pmol of labeled (avidin-HRP complex) detection probe PPNG-C was added to the hybridization solution bound to magnetic micro particles with and without the preservative reagent at 37° C. for 1 hour. The control and treated probes were then added to the amplification product and the reaction was colorimetrically detected at $A_{450\ nm}$. The signal obtained from the hybridization probes treated with a reagent of the invention was found to be significantly higher than the untreated probes.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims. The contents of all references, issued patents, and published patent applications cited throughout this application are hereby incorporated by reference.

What is claimed is:

1. A method of preserving a nucleic acid in a bodily fluid, comprising the steps of:
   a) providing a nucleic acid preservative solution comprising
      i) an amount of a divalent metal chelator selected from the group consisting of etbylenediaminetetraacetic acid (EDTA), [ethylenebis(oxyethylenenitrilo)]tetraacetic acid (EGTA) and 1,2-bis(2-aminophenoxy)ethane-N,N,N',N'-tetraacetic acid (BAPTA), or salts thereof in the range of about 0.001M to about 0.1M; and
      ii) an amount of at least one chelator enhancing component selected from the group consisting of lithium chlorides guanidine, sodium salicylate, sodium perchlorate and sodium thiocyanate in the range of about 0.1M to about 2M; and
   b) adding said nucleic acid preservative solution to said bodily fluid, thus preserving said nucleic acid.

2. The method of claim 1 wherein said nucleic acid preservative solution is an aqueous solution comprising said divalent metal chelator and said chelator enhancing component.

3. The method of claim 1 wherein said chelator enhancing component is selected from the group consisting of sodium perchlorate, sodium thiocyanate, and lithium chloride.

4. The method of claim 1 wherein said chelator enhancing component is present in an amount of about 1M.

5. The method of claim 1 wherein said divalent metal chelator is present in an amount of at least 0.01M.

6. The method of claim 1 wherein said nucleic acid preservative solution further comprises an amount of at least one enzyme inactivating component selected from the group consisting of manganese chloride, sarkosyl, and sodium dodecyl sulfate.

7. The method of claim 1 wherein said nucleic acid is selected from the group consisting of DNA, RNA, mRNA, and cDNA.

8. The method of claim 7 wherein said DNA is eukaryotic DNA.

9. A preserved nucleic acid-containing fluid comprising:
   a) an amount of a divalent metal chelator selected from the group consisting of ethylenediaminetetraacetic acid (EDTA), [ethylenebis(oxyethylenenitrilo)]tetraacetic acid (EGTA) and 1,2-bis(2-aminophenoxy)ethane-N,N,N',N'-tetraacetic acid (BAPTA), or salts thereof in the range of about 0.001M to about 0.1M;
   b) an amount of at least one chelator enhancing component selected from the group consisting of lithium chloride, guanidine, sodium salicylate, sodium perchlorate, and sodium thiocyanate in the range of about 0.1M to about 2M; and
   c) a bodily fluid obtained from a human subject.

10. The preserved nucleic acid-containing fluid of claim 9, wherein said bodily fluid obtained from a human subject is urine.

11. The preserved nucleic acid-containing fluid of claim 9, wherein said bodily fluid obtained from a human subject is blood.

12. The preserved nucleic acid-containing fluid of claim 9, wherein said bodily fluid obtained from a human subject is blood serum.

13. The preserved nucleic acid-containing fluid of claim 9, wherein said bodily fluid obtained from a human subject is amniotic fluid.

14. The preserved nucleic acid-containing fluid of claim 9, wherein said bodily fluid obtained from a human subject is spinal fluid.

15. The preserved nucleic acid-containing fluid of claim 9, wherein said bodily fluid obtained from a human subject is conjunctival fluid.

16. The preserved nucleic acid-containing fluid of claim 9, wherein said bodily fluid obtained from a human subject is salivary fluid.

17. The preserved nucleic acid-containing fluid of claim 9, wherein said bodily fluid obtained from a human subject is vaginal fluid.

18. The preserved nucleic acid-containing fluid of claim 9, wherein said bodily fluid obtained from a human subject is stool.

19. The preserved nucleic acid-containing fluid of claim 9, wherein said bodily fluid obtained from a human subject is seminal fluid.

20. The preserved nucleic acid-containing fluid of claim 9, wherein said bodily fluid obtained from a human subject is sweat.

21. A specimen container containing the preserved nucleic acid-containing fluid of claim 9.

22. A specimen container containing the preserved nucleic acid-containing fluid of any one of claims 10–20.

* * * * *

SEQUENCE LISTING

<160> NUMBER OF SEQ ID NOS: 3

<210> SEQ ID NO 1
<211> LENGTH: 17
<212> TYPE: DNA
<213> ORGANISM: Homo sapiens

<400> SEQUENCE: 1
agttatctac acgacgg                                                    17

<210> SEQ ID NO 2
<211> LENGTH: 17
<212> TYPE: DNA
<213> ORGANISM: Homo sapiens

<400> SEQUENCE: 2
ggcgtactat tcactct                                                    17

<210> SEQ ID NO 3
<211> LENGTH: 25
<212> TYPE: DNA
<213> ORGANISM: Homo sapiens

<400> SEQUENCE: 3
gcgtcagacc cctatctata aactc                                           25